United States Patent
Cabelka et al.

(10) Patent No.: US 9,655,851 B2
(45) Date of Patent: May 23, 2017

(54) GRANULAR MATERIAL FOR DOSAGE FORMS

(71) Applicant: Dow Global Technologies LLC, Midland, MI (US)

(72) Inventors: Tim D. Cabelka, Midland, MI (US); Akshay Bellare, Hillsborough, NJ (US); Ka Chun A. Chan, Midland, MI (US); Tina P. Dasbach, Midland, MI (US); Kacee B. Ender, Missouri City, TX (US); Karl V. Jacob, Midland, MI (US); Robert E. Scheid, Jr., North Wales, PA (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/316,879

(22) Filed: Jun. 27, 2014

(65) Prior Publication Data

US 2014/0308356 A1   Oct. 16, 2014

Related U.S. Application Data

(62) Division of application No. 12/595,627, filed as application No. PCT/US2008/055274 on Feb. 28, 2008, now Pat. No. 8,877,249.

(Continued)

(51) Int. Cl.
| | | |
|---|---|---|
| *A61K 9/16* | (2006.01) | |
| *A61K 31/55* | (2006.01) | |
| *A61K 31/138* | (2006.01) | |

(52) U.S. Cl.
CPC .......... *A61K 9/1652* (2013.01); *A61K 31/138* (2013.01); *A61K 31/55* (2013.01); *Y10T 428/2982* (2015.01)

(58) Field of Classification Search
None
See application file for complete search history.

(56) References Cited

U.S. PATENT DOCUMENTS

| 4,159,345 A | 6/1979 | Takeo et al. |
| 4,734,285 A | 3/1988 | Alderman |

(Continued)

FOREIGN PATENT DOCUMENTS

| DE | 19725911 | 12/1998 |
| EP | 0835881 B1 | 2/2001 |
| JP | 200063565 | 2/2000 |

OTHER PUBLICATIONS

Dow® "Using Dow Excipients for Controlled Release of Drugs in Hydrophilic Matrix Systems", published Sep. 2006, accessed at http://msdssearch.dow.com/PublishedLiteratureDOWCOM/dh_0379/0901b803803797ad.pdf?filepath=methocel/pdfs/noreg/198-02075.pdf&fromPage=GetDoc.*

(Continued)

*Primary Examiner* — Carlos Azpuru
*Assistant Examiner* — Casey Hagopian (57) ABSTRACT

A granular material which has
   a mean particle diameter of 150 to 800 micrometers; and
   an unsettled bulk density of 0.1 to 0.35 g/cm3 and/or a compactibility which results in a compact with a tensile strength of at least 1.7 MPa when the granular material is subjected to a compaction pressure of 266 MPa; and
   wherein the main component of the granular material is a cellulose derivative or an alkylene oxide homo- or copolymer or a blend thereof
is useful for preparing dosage forms with a controlled release profile.

13 Claims, 3 Drawing Sheets

Related U.S. Application Data (60) Provisional application No. 60/923,446, filed on Apr. 13, 2007.

(56) References Cited

U.S. PATENT DOCUMENTS

| | | | |
|---|---|---|---|
| 5,126,145 | A | 6/1992 | Evenstad |
| 5,273,758 | A | 12/1993 | Royce |
| 6,117,451 | A * | 9/2000 | Kumar .................... 424/465 |
| 6,617,353 | B1 * | 9/2003 | Ito et al. ................. 514/557 |
| 6,858,725 | B1 * | 2/2005 | Vladyka et al. ........... 536/56 |
| 2003/0017198 | A1 | 1/2003 | Yeh et al. |
| 2004/0209080 | A1 | 10/2004 | Hayakawa et al. |

OTHER PUBLICATIONS

Sigma Aldrich® "Particle Size Conversion Table", 2004, accessed online at http://www.sigmaaldrich.com/chemistry/stockroom-reagents/learning-center/technical-library/particle-size-conversion.printerview.html.*

Int. J. of Pharmaceutics, 1993,100, p. 241-248, Properties of hydroxypropylmethylcellulose granules produced by water spraying, Liu et al.

Int. J. of Pharmaceutics, 2006, 313, p. 57-65, Initial studies of water granulation of eight grades of hypromellose (HPMC), Herder et al.

Campos-Aldrete, et al., Influence of the Viscosity Grade and the Particle Size of HPMC on Metronidazole Release from Matrix Tablets, Europ. J. Pharma. and Biopharma., 43, 1997, pp. 173-178.

Mitchell, et al., The Influence of the Particle size of Hydroxypropylmethylcellulose K15M on its hydration and performance in Matrix Tablets, International Journal of Pharmaceutics, 100, 1993, 175-179.

Communication received from the European Patent office regarding European application No. 08730949.8 dated Jan. 20, 2015.

* cited by examiner

GRANULAR MATERIAL FOR DOSAGE FORMS

FIELD OF THE INVENTION

This invention relates to a granular material which is useful as an excipient for a dosage form, particularly for a pharmaceutical dosage form, and to a dosage form comprising the granular material and an active ingredient. More particularly, the present invention relates to a free-flowing directly compressible granular material which can be blended with an active ingredient and directly compressed into a dosage form.

BACKGROUND OF THE INVENTION

Sustained release dosage forms have found wide usage in a variety of technology areas, such as in personal care or agricultural applications, water treatment and particularly in pharmaceutical applications. Sustained release dosage forms are designed to release a finite quantity of a compound into an aqueous environment over an extended period of time. Known sustained release pharmaceutical dosage forms contain a medicament or a vitamin whose rate of release is controlled by a polymeric matrix. Sustained release pharmaceutical dosage forms are desirable because they provide a method of delivering a long-lasting dose in a single application without overdosing. U.S. Pat.No. 4,734,285 discloses that the release of an active composition from a solid tablet can be prolonged by employing a fine particle sized hydroxypropyl methylcellulose ether composition. The particle size of the hydroxypropyl methylcellulose ether is so small that at least 90 percent by weight of the cellulose ether particles pass through a 100 mesh screen, and preferably at least 97 percent by weight of the cellulose ether particles pass through a 140 mesh screen to achieve a long release profile. While such hydroxypropyl methylcellulose ether particles provide excellent release profiles to tablets, these particles of very small size are known to be of poor flowability and to increase the risk of dust inhalation or dust explosions.

In order to prepare solid, shaped dosage forms from powders, it is generally necessary to process the powders in a manner to improve their flowability and other characteristics which will enable the resulting material to be fabricated by conventional processes such as tableting, encapsulation, molding, etc. into a satisfactory unit form that can suitably deliver an active substance, such as a therapeutic agent, into the environment of use.

Various processes have therefore been developed for modifying powders or other particulate materials, in which typically the powders are gathered together with a binder material into larger permanent free-flowing agglomerates or granules referred to collectively as a "granulation." Granular materials provide the benefits of improved dry flow properties, reduced dusting and in many cases increased dispersibility when preparing solutions.

For example, solvent-assisted "wet" granulation processes are generally characterized in that the powders are combined with a binder material and moistened with water or an organic solvent under conditions that result in formation of a wet granulated mass from which the solvent must then be evaporated. Such processes, while widely employed, have certain recognized limitations, for example in connection with moisture or heat sensitive medicaments or other actives. Alternatively, the known "dry granulation" processes, which can depend on fairly complicated milling schemes to produce a suitable granulation, also have acknowledged disadvantages.

A direct compression process can provide a simpler and more economical means of preparing compressed dosage forms. In such a process, the active ingredient, such as biologically active ingredients like vitamins, herbal and mineral supplements and drugs, is combined with an excipient, i.e., a substance which does not serve as an active ingredient and does not have a therapeutic effect, but is used as a diluent, vehicle or binder for the active ingredient and which itself is characterized in having the requisite properties for tableting, such as flowability, appropriate particle size distribution, binding ability, acceptable bulk and tap density and/or dissolution properties. The resulting blend can therefore be directly provided to a die cavity or mold for compaction, without prior granulation. See Shangraw, "Compressed Tablets by Direct Compression," in Pharmaceutical Dosage Forms, 2d Ed., 1989, Vol. 1, pp. 195-246. The resulting compressed dosage form generally provides the requisite stability, dissolution or disintegration properties, tablet-to-tablet and batch uniformity and other desirable characteristics of solid dosage forms.

Materials employed by the art which to varying degrees fulfill the requirements of a direct compression vehicle include water soluble materials e.g., various forms of lactose, such as spray-dried lactose, Fast Flow (Trademark) lactose, or anhydrous lactose, as well as sucrose, dextrose, sorbitol, mannitol and maltodextrin, and relatively insoluble materials such as microcrystalline cellulose, such as Avicel (Trademark), starch, dicalcium phosphate dihydrate, and calcium carbonate. U.S. Pat. No. 5,237,758 discloses the use of directly compressible polyethylene oxide vehicles for preparing directly compressible therapeutic dosage forms. U.S. Pat. No. 4,159,345 discloses the use of a microcrystalline cellulose having an average degree of polymerization of 60 to 375, an apparent specific volume of 1.6 to 3.1 cc/g, and a repose angle of 35 to 42° as an excipient in high-speed direct compression. Furthermore, it is known to use fumed silica as a glidant in tablet and capsule formulations to promote the flow of powders.

One object of the present invention is to provide a granular material which has good flowability and which is useful as an excipient for dosage forms, particularly for preparing tablets of suitable hardness. A preferred object of the present invention is to provide a granular material which is useful as an excipient for dosage forms and which has the combined properties of good flowability and the ability to delay and/or control (sustain) the release of an active ingredient from the dosage form. An even more preferred object of the present invention is to provide a granular material which is useful as an excipient for a dosage form, which has the above-mentioned properties of good flowability and ability of sustained release and which is useful in a direct compression process for producing dosage forms.

SUMMARY OF THE INVENTION

Accordingly, one aspect of the present invention is a granular material having a mean particle diameter of 150 to 800 micrometers and a compactibility resulting in a compact with a tensile strength of at least 1.7 MPa when the granular material is subjected to a compaction pressure of 266 MPa, the main component of the granular material being a cellulose derivative, an alkylene oxide homo- or copolymer or a blend thereof.

Another aspect of the present invention is granular material having a mean particle diameter of 150 to 800 micrometers and an unsettled bulk density of 0.1 to 0.35 g/cm³, the main component of the granular material being a cellulose derivative, an alkylene oxide homo- or copolymer or a blend thereof.

Yet another aspect of the present invention is a starting material for a dosage form which comprises an above-mentioned granular material and an active ingredient.

Yet another aspect of the present invention is a dosage form which has been produced from a composition comprising an above-mentioned granular material and an active ingredient.

Yet another aspect of the present invention is a direct compression process for preparing a dosage form which comprises the step of a.) blending an active ingredient, an above-mentioned granular material and one or more optional adjuvants in the absence of a substantial amount of added solvent or heat, and b.) compressing the resulting composition to a dosage form.

Yet another aspect of the present invention is the use of the above-mentioned granular material for producing a dosage form.

Yet another aspect of the present invention is a process for granulating a polymer powder which comprises the step of granulating in a fluid bed granulator a cellulose derivative, an alkylene oxide homo- or copolymer or a blend thereof to produce an above-mentioned granular material.

DETAILED DESCRIPTION OF THE INVENTION

The granular material of the present invention has a mean particle size diameter of at least 150 micrometers, preferably at least 200 micrometers, more preferably at least 250 micrometers. Its mean particle size diameter is up to 800 micrometers, preferably up to 500 micrometers, and more preferably up to 350 micrometers. The term "mean particle size" as used herein means the D[4,3], also designated as equivalent volume mean. $D[4,3]=\Sigma d^4/\Sigma d^3$, wherein the diameter d of a particle is the diameter of a sphere having the same volume as the volume of a given particle. The D[4,3] or equivalent volume mean is preferably measured using a RapidVue 5× image analyzer which is commercially available from Beckman Coulter, Inc., California.

The granular material of the present invention has a good compactibility. Compactibility is defined by Alderborn and Nystrom (*Pharmaceutical Powder Compaction Technology*, Marcel Dekker, New York, 1996) as the ability of a powder bed to cohere into or to form a compact under a compressive force. In one aspect of the present invention the granular material has a compactibility such that when the granular material is subjected to a compaction pressure of 266 MPa a compact is produced with a tensile strength of at least 1.7 MPa. Preferably the granular material has a compactibility which results in a compact with a tensile strength of at least 2.0 MPa, more preferably at least 2.3 when the granular material is subjected to a compaction pressure of 266 MPa. Generally the compactibility of the granular material of the present invention is such that a compact with a tensile strength of up to 5 MPa, typically up to 4 MPa, in most cases up to 3.5 MPa results when the granular material is subjected to a compaction pressure of 266 MPa. A compaction pressure of 266 MPa (5000 pounds force applied to a 10.3 mm diameter tablet punch) is a pressure that is typically applied in processes for manufacturing tablets. The tensile strength of a compact, when formed by a pressure typically used in the manufacturing process is an indication of the compactibility of the granular material. By the term "tensile strength" the breaking strength is meant, that means the stress coordinate on the stress-strain curve at the point of rupture. The tensile strength can be calculated according to the following formula: Tensile Strength=$2P/(\pi)(t)(D)$, where P=applied load, t=thickness of compact in mm, and D=diameter of the compact in mm The applied load is the force at the breaking point of the compact, converted into N (Newtons). (1 N/mm²=1 MPa; $\pi$=3.14159). The applied load, i.e. the force at the breaking point of the compact, is preferably measured by a HT-300 Hardness Tester.

When the tensile strength y of the produced compact is expressed as a function of the compaction pressure x to which the granular material of the present invention is subjected, typically a straight line is obtained. The observed slope is another indication of the good compactibility of the granular material of the present invention In another aspect of the present invention the granular material has an unsettled bulk density of from 0.1 to 0.35 g/cm³, preferably from 0.15 to 0.30 g/cm³, more preferably from 0.15 to 0.25 g/cm³. The unsettled bulk density is preferably measured using a Scott Volumeter, for example as described in the United States Pharmacopeia 30, article <616> Bulk Density and Tapped Density, Method II. Material is poured into a funnel, through a baffled column and into a metal cylinder with a known volume. Material is poured into the apparatus until the cylinder overflows with material. Excess powder is scraped off the top using a spatula. The cylinder is then weighed and the bulk density calculated.

Preferably, the granular material of the present invention has the above-described compactibility and unsettled bulk density in combination. The Applicants believe that an unsettled bulk density in the above-mentioned range contributes to the good compactibility of the granular material of the present invention.

The granular material of the present invention generally has a particle size distribution span of from 0.75 to 4, preferably from 0.75 to 3, more preferably from 0.9 to 2.5, most preferably from 1 to 2, preferably determined by using an image analysis technique with a RapidVue 5× image analyzer which is commercially available from Beckman Coulter, Inc., California. Without wanting to be bound by the theory, Applicants believe that a particle size distribution span within the above-mentioned range contributes to a unique balance of properties which are highly preferred for excipients for sustained-release dosage forms, particularly for excipients to be used in a direct compression process, such as flow of the granular material, good compactibility of the granular material leading to strong, hard tablets, with small variability in tablet-to-tablet physical properties, in combination with reproducible kinetics of the sustained release of the active ingredient. The particle size distribution span is defined as [(d90-d10)/d50], wherein dn is the diameter where n mass percent of the particles have a smaller equivalent diameter and (100-n) mass percent have a larger equivalent diameter. For example, d90 is the diameter where 90 mass percent of the particles have a smaller equivalent diameter and the other 10 mass percent have a larger equivalent diameter. The equivalent particle diameter d is the diameter of a sphere having the same volume as the volume of a given particle.

Alternatively the particle size distribution span can be determined by sieve analysis using sieves of different screen sizes. Advantageously sieves of 8 mesh (screen size 2360 micrometers), 12 mesh (screen size 1700 micrometers), 16 mesh (screen size 1180 micrometers), 20 mesh (screen size 850 micrometers), 30 mesh (screen size 600 micrometers), 40 mesh (screen size 425 micrometers), 50 mesh (screen size 300 micrometers), 70 mesh (screen size 212 micrometers) 100 mesh (screen size 150 micrometers), 140 mesh (106 micrometers), 200 mesh (screen size 75 micrometers) and 325 mesh (screen size 45 micrometers) respectively are used for determining the particle size distribution span of the granular material of the present invention. The cumulative mass percent of material passing a given screen size is determined The data is then plotted as the cumulative mass percent of material passing versus a given screen size and is used to determine the particle size distribution span of the granular material of the present invention. The particle size distribution span determined by sieve analysis is defined as [(d'90-d'10)/d'50], wherein d'n is the diameter where n mass percent of the particles have a smaller diameter and (100-n) mass percent have a larger diameter. For example, d'90 is the diameter where 90 mass percent of the particles have a smaller diameter and the other 10 mass percent have a larger diameter, as determined by sieve analysis.

The granular material of the present invention preferably has an average aspect ratio of from 1 to 2, more preferably from 1.4 to 1.9, most preferably from 1.6 to 1.8. The aspect ratio of a particle is defined as the ratio of the length to width of a least bounding rectangle. A least bounding rectangle is the rectangle shape which has the smallest area that completely encloses the particle. For example, a particle which can be bound by a square has an aspect ratio of one. The average aspect ratio as defined herein is the ratio of the average length to the average width of the particles. The average aspect ratio is preferably measured using a Rapid-Vue 5× image analyzer which is commercially available from Beckman Coulter, Inc., California.

The granular material of the present invention is useful as an excipient for a dosage form, particularly as an excipient for a sustained-release dosage form, which means that it has the function to regulate the release an active ingredient from the dosage form over an extended period of time. The term "sustained-release" is used herein synonymously to the terms prolonged release; extended release; sustained release; depot release; time release; controlled release; modified release or prolonged action. "Sustained release" is an approach by which active compounds, such as biologically active compounds, are made available at a rate and duration designed to accomplish an intended effect. For example, an oral controlled release drug delivery system is a device or dosage form that regulates the release of a drug into the gastrointestinal tract, thereby controlling the absorption rate of that drug in order to achieve a desired blood plasma profile. These dosage forms are designed to provide a constant or nearly constant drug level in plasma with reduced fluctuation via a slow, continuous release of drug over an extended period of time. In the sustained-release dosage form of the present invention it generally takes between 0.75 and 36 hours, more preferably between 4 and 30 hours, and most preferably between 8 and 24 hours to release the active ingredient from the dosage form.

The granular material of the present invention is useful as an excipient for dosage forms, particularly for sustained-release dosage forms in a variety of technological fields, for example in personal care, laundry care or agricultural applications, water treatment, and particularly in human or animal health care applications, most specifically pharmaceutical applications wherein a biologically active ingredient is selected from vitamins, herbal and mineral supplements and drug substances.

The main component of the granular material is a cellulose derivative or an alkylene oxide homo- or copolymer or a blend thereof. The cellulose derivative or alkylene oxide homo- or copolymer is preferably water-soluble, that means it preferably has a solubility in water of at least 2 grams, more preferably at least 3 grams, most preferably at least 5 grams in 100 grams of distilled water at 25° C. and 1 atmosphere. The cellulose derivative or alkylene oxide homo- or copolymer generally has a lower limit for the weight average molecular weight of at least 20,000, preferably at least 60,000, more preferably at least 80,000. The preferred upper limit for the weight average molecular weight largely depends on the type of polymer, the physicochemical properties of the active ingredient to be released and the desired amount of time over which the active ingredient is to be released. To achieve optimum sustained release properties the cellulose derivative or alkylene oxide homo- or copolymer preferably has a weight average molecular weight from approximately 100,000 to as much as 10,000,000. The aforementioned ranges are meant for illustrative purposes, they are not intended to limit useful application of the cellulose derivatives or alkylene oxide homo- or copolymers.

Preferred alkylene oxide homo- and copolymers are ethylene oxide homo- and copolymers. The term "cellulose derivative" does not include unmodified cellulose itself. Preferred cellulose derivatives are water-soluble cellulose esters or cellulose ethers. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, mixed $C_1$-$C_3$-alkyl celluloses, such as methyl ethyl celluloses, or alkoxy hydroxyethyl hydroxypropyl celluloses, the alkoxy group being straight-chain or branched and containing 2 to 8 carbon atoms. The more preferred cellulose ethers are methylcellulose, methyl ethyl cellulose, hydroxyethyl cellulose, hydroxyethyl ethylcellulose, hydroxypropyl cellulose, hydroxyethylmethyl cellulose, hydroxypropyl methylcellulose, and carboxymethyl cellulose, which are classified as water-soluble cellulose ethers by the skilled artisans. The most preferred water-soluble cellulose ethers are hydroxypropyl methylcelluloses with a $DS_{methoxyl}$ of from 0.9 to 2.8, preferably from 1.12 to 2.04, and a $MS_{hydroxypropoxyl}$ of from 0.01 to 1.14, preferably from 0.1 to 0.34. Methylcellulose and hydroxypropyl methylcellulose (hypromellose) can be analyzed in accordance with the procedures given in the respective monographs of the Unites States Pharmacopeia (current edition). Hydroxypropyl methylcelluloses, such as METHOCEL K100M, METHOCEL K4M, METHOCEL K15M, and METHOCEL E4M hydroxypropyl methylcellulose are commercially available from The Dow Chemical Company. Particularly useful cellulose derivatives are hydroxypropyl methylcelluloses having a hydroxypropoxyl substitution of from 0.5 to 32 percent and a methoxyl substitution of from 16 to 32 percent, more preferably having a hydroxypropoxyl substitution of from 4 to 32 percent and a methoxyl substitution of from 16.5 to 30 percent, and most preferably having a hydroxypropoxyl substitution of from 4 to 12 percent and a methoxyl substitution of from 19 to 30 percent. The water-soluble cellulose derivative generally has a viscosity of from 5 to 2,000,000 cps (=mPa·s), preferably from 50 cps to 200,000 cps, and most preferably from 100 to 100,000 cps, preferably measured as a two weight percent aqueous solution at 20 degrees Celsius using a capillary viscometer. Alternatively, the viscosity can be measured in a rotational viscometer.

Generally at least 60 percent, preferably at least 80 percent, more preferably at least 90 percent, most preferably at least 98 percent of the granular material of the present invention is a cellulose derivative or an alkylene oxide homo- or copolymer or a blend thereof. The granular material may comprise minor amounts of an adjuvant, such as a binder or residues of a liquid like water which may have been used to prepare the granular material of the present invention, but the amount of such adjuvant is generally not more than 40 percent, preferably not more than 20 percent, more preferably not more than 10 percent, and most preferably not more than 2 percent, based on the total weight of the granular material of the present invention.

However, it should be noted that a dosage form can comprise one or more excipients and/or adjuvants in addition to the granular material of the present invention. The dosage form preferably comprises such an amount of the granular material of the present invention that the amount of cellulose derivative or alkylene oxide homo- or copolymer or a blend thereof is from 10 to 60 percent, more preferably from 15 to 50 percent, most preferably from 25 to 40 percent, based on the total weight of the pharmaceutical dosage form.

The granular material of the present invention can be obtained by subjecting a cellulose derivative or an alkylene oxide homo- or copolymer or a blend thereof in powder form to a granulation step and selecting those portions of the obtained particles which have the above-mentioned combination of product parameters. Various granulation methods are known in the art, for example extrusion, dry granulation such as roller compaction, or, preferably, wet-granulation processes. The polymer in powder form which is used in the granulation generally has a mean particle diameter of less than 150 micrometers, in most cases less than 120 micrometers.

A number of granulation processes are known in the art and are frequently categorized by the magnitude of the shear forces that are exerted on the powder bed being granulated. For example, so-called "low shear granulation" is usually accomplished using planetary mixers, in which vertical mixing blades rotate through the powders at relatively slow speeds. Somewhat greater (i.e., "medium") shear forces can be produced in granulation equipment in which the powders are confined in a cylindrical shell and the powders are agitated in the presence of a granulating liquid, which may or may not contain a binder, by ribbon-type blades. "High shear granulation" is typically performed in equipment in which a main agitator or impeller applies high shear and compaction forces to the powders through the combination of "plowshare" type blades and the relatively high rotation rates at which they move; in addition, the equipment generally also features a smaller, independently controlled, high speed chopper which is designed to break up large lumps produced during the granulation process. The chopper also helps to more fully incorporate the granulating liquid into the material as it is introduced to the mixing vessel, typically through a spray nozzle. A specific type of high shear granulators are referred to as "Lödige granulators" after the name of the first commercial equipment. The Lödige granulators are provided with specially-designed ploughshare blades and high-speed choppers. The desired portions of the obtained particles can be selected by known particle-particle separation techniques, for example, by sieving or screening.

A particularly useful process for obtaining the granular material of the present invention is fluid bed granulation, also called fluidized bed granulation. In this process a binding liquid is sprayed into or on a bed of fluidized powder. Preferably the binding liquid is atomized by compressed air, for example in a binary nozzle before spraying it into or on the bed of fluidized powder. The powder is fluidized in a known manner, for example by a gas flowing vertically through a distributor plate in the base of a processing vessel. The binding liquid generally is water, an organic solvent or a mixture thereof which optionally comprises a binder or a surfactant. Useful organic liquids are alcohols, preferably monofunctional alcohols, such as ethanol; alkenes, alkanes, halogenated alkenes, halogenated alkanes, ethers, esters or oils, such as paraffin oils, animal oils or vegetable oils. Most preferably, the binding liquid is water. Useful binders or surfactants are known in the art. Their amount, if present, preferably is from 0.5 to 10 percent, more preferably from 1 to 5 percent, based on the weight of the liquid. If a binder is used, it is particularly preferred to use a polymeric binder of the same type of cellulose derivative or alkylene oxide homo- or copolymer as the granular material. The skilled artisan knows how to select the polymer weight and the polymer concentration in the liquid to obtain a sprayable solution. Generally the weight ratio between the polymer in powder form and the binding liquid is from 0.33 to 0.005:1, preferably from 0.25 to 0.01:1, more preferably from 0.18 to 0.02:1. These weight ratios are particularly useful when the binding liquid is water.

It has surprisingly been found that the use of a fluidized bed granulation process for obtaining the granular material of the present invention has significant advantages over other granulation processes. A fluidized bed granulation process provides an granular material of the present invention with a unique balance of properties which are important for excipients for sustained-release dosage forms, particularly for excipients to be used in a direct procession process, such as flow of the granular material, good compactibility of the granular material leading to strong, hard tablets, with small variability in tablet-to-tablet physical properties, in combination with reproducible kinetics of the sustained release of the active ingredient. The granular material of the present invention can be obtained by the fluid bed granulation process in an efficient manner without having to do an undue amount of screening/sieving after granulation. This unique balance of properties is particularly important for excipients for sustained-release pharmaceutical dosage forms.

Applicants have found that a fluid bed granulation process can be used to obtain an granular material of the present invention which has a narrow particle size distribution span.

The particle size distribution span is determined as described in detail above. It has surprisingly been found that the granular material obtained by fluid bed granulation has a significantly more narrow particle size distribution span than granular material obtained by other granulation processes, such as high shear granulation. Surprisingly it has also been found that the granular material obtained by fluid bed granulation has a much narrower particle size distribution span than granular material obtained by Lödige granulation. Without wanting to be bound by the theory, Applicants believe that the narrow particle size distribution span that is obtained by the fluid bed granulation process of the present invention contributes to the above-mentioned unique balance of properties.

Applicants have also found that a fluid bed granulation process can be used to obtain a granular material of the present invention which has a good compactibility. It has been found that a fluid bed granulation process can be used to obtain a granular material of superior compactibility relative to a comparative granular material that has been produced by high shear granulation processes. In particular is has been found that a fluid bed granulation process can be used to obtain a granular material of considerably superior compactibility relative to a comparative granular material that has been produced by Lödige granulation. It has also been found that the superior compactibility of the granular material carries over into dosage forms, such as tablets, which are produced from a composition comprising an active ingredient, the granular material and one or more optional adjuvants. Compressed dosage forms, such as tablets, have a higher hardness (also known as diametral crushing strength) when the granular material of the present invention is used. Those skilled in the art typically quantify the mechanical properties of compressed tablets in terms of hardness or crushing strength.

The above-described granular material has a unique combination of features which makes it very useful as an excipient in dosage forms, for example in pharmaceutical dosage forms. The granular material has good flow properties. It can be efficiently blended with a biologically active ingredient, and, if desired, with one or more optional adjuvants, even in the absence of a substantial amount of added solvent or heat. It is to be understood that one or more types of the above-described granular material and one or more types of an active ingredient can be blended with one or more optional adjuvants to prepare a dosage form. Preferably the blending process is conducted at about room temperature.

A large variety of active ingredients are useful, dependent on the intended end-use of the dosage form. Active ingredients are known in the art and include, among others, detergents or surfactants for laundry care applications; fertilizers, herbicides or pesticides in formulations designed to release the bioactive agents over a prolonged period of time in agricultural applications. A wide range of biologically active ingredients are useful, such as vitamins, herbals and mineral supplements and drugs. The biologically active ingredient includes hydrophobic, hydrophilic and amphiphilic compounds. The biologically active ingredient may be used for treating indications such as, by way of example and without limitation, inflammation, gout, hypercholesterolemia, microbial infection, AIDS, tuberculosis, fungal infection, amoebic infection, parasitic infection, cancer, organ rejection, diabetes, heart failure, arthritis, asthma, pain, congestion, urinary tract infections, vaginal infection, seizure-related disorders, depression, psychosis, convulsion, diabetes, blood coagulation, hypertension and birth control. The amount of the biologically active ingredient loaded into a pharmaceutical dosage form will vary according to the pharmacological activity of the compound, the indication being treated, the targeted dosing regimen, the projected method of administration, the integrity or stability of the final composition or other such reasons.

The amount of the active ingredient generally is at least 0.5 percent, preferably at least 1 percent, more preferably at least 5 percent, most preferably at least 10 percent, based on the total weight of the dosage form, and generally up to 75 percent, preferably up to 65 percent, more preferably up to 55 percent, most preferably up to 45 percent, based on the total weight of the dosage form. The active ingredient is generally solid and preferably has a mean particle size diameter as defined further above of from 1 to 500 micrometers. Useful optional adjuvants are known in the art and are generally solid, such as one or more fillers, pigments, colorants, flavorants, disintegrating agents, binders, plasticizers, salts, acidic and basic pH modifiers, antioxidants and/or lubricants. Examples of such adjuvants are acacia, corn starch, guar gum, potato starch, alginic acid, stearic acid, magnesium stearate, lactose, sucrose, dicalcium phosphate, microcrystalline cellulose, sugars, minerals, cellulose powder or cellulose fibers. Optional adjuvants are generally solid and preferably have a mean particle size diameter as defined further above of from 1 to 500 micrometers.

The blend of one or more types of granular materials of the present invention, one or more active ingredients and one or more optional adjuvants has good flow properties and exhibits a minimum of segregation, which means that the blend shows excellent uniformity. By this it is meant that if the blend is divided into portions, the content of the active ingredient is essentially the same in all portions. The blend can be directly filled into capsules or can be subjected to a direct compression process to produce tablets or similar dosage forms. The efficient feeding of the blend to a capsule filling device or to a compression device allows for uniform weights of the dosage forms. The combination of good powder flow, minimum segregation and good compactibility allows the blend to be efficiently processed to a dosage form in a direct compression process, even in the absence of a substantial amount of added solvent, heat, or additional processing steps. By the term "in the absence of a substantial amount of added solvent or heat" is meant that solvent or heat is not added in a sufficient amount to the blend of the active ingredient and the granular material to effect further granulation of the blend. Preferably the direct compression process is conducted in the absence of any amount of added solvent or heat.

Direct compression processes to produce tablets are known in the art. Typically a compaction pressure of from 150 MPa to 375 MPa is sufficient to produce tablets of good quality. The direct compression process of the present invention eliminates the need for formulators of dosage forms to subject the blend of one or more active ingredients and one or more excipients to a wet granulation step before compressing the blend to a tablet. A wet granulation step involves wetting, drying and screening steps, which is not desirable for moisture-sensitive or heat-sensitive drugs. The direct compression process of the present invention also eliminates the need for a complicated dry-granulation process. In addition, products made by the direct compression process are less costly than those produced when wet or dry granulation processes are employed.

It has surprisingly been found that sustained release pharmaceutical dosage forms with excellent drug release profiles can be produced even if the granular material has a considerably larger mean particle size than that recommended for sustained release pharmaceutical dosage forms in U.S. Pat. No. 4,734,285.

The granular material can also be used as a coating, particularly as a compression coating, of a dosage form to control the release of the active ingredient. However, more preferably the granular material forms at least a portion of the matrix of a dosage form.

The present invention is further illustrated by the following examples which are not to be construed to limit the scope of the present invention. Unless otherwise mentioned all parts and percentages are by weight.

COMPARATIVE EXAMPLE A AND EXAMPLE 1

The mean particle diameter, the average aspect ratio and the particle size distribution span of the hydroxypropyl methylcellulose specified below are measured using a RapidVue 5× image analyzer which is commercially available from Beckman Coulter, Inc., California.

Excipient of Comparative Example A

A hydroxypropyl methyl cellulose which is commercially available from The Dow Chemical Company under the Trademark METHOCEL K4M Premium CR Grade is used in Comparative Example A. The hydroxypropyl methylcellulose has a methoxyl content of 19-24 percent, a hydroxypropoxyl content of 7-12 percent, a nominal viscosity of about 4000 mPa·s, and the physical properties listed in Table 1 below. This non-granulated hydroxypropyl methylcellulose of fine particle size is known to be useful as an excipient for pharmaceutical controlled release tablets.

Production of Granular Material of Example 1

The hydroxypropyl methylcellulose described in Comparative Example A is granulated in a fluid bed granulator using water as a granulating fluid. About 28% water is used, based on the weight of hydroxypropyl methylcellulose. A Glatt, model GPCG-300, fluid bed system is used for granulation. The Glatt granulator is a conical fluid bed system with an integral fan, air heater, spray nozzle, and dust collector. The granulated hydroxypropyl methylcellulose has the physical properties listed in Table 2 below. The use of the granular material of the present invention as an excipient for pharmaceutical controlled release tablets is tested.

Preparation of the Blends of Example 1 and of Comparatived Example A

The excipients of Comparative Example A and of Example 1 are dry blended with other ingredients as listed in Tables 1 and 2 below in a V-blender for 10 minutes to prepare a pharmaceutical composition.

TABLE 1

Comparative Example A

| Ingredients | Manufacturer | Wt. % |
|---|---|---|
| METHOCEL K4M Premium CR Grade of Comparative Example A | The Dow Chemical Company, USA | |
| Properties of METHOCEL K4M Premium CR | | |
| mean particle diameter | 100 micrometers* | |
| particle size distribution span | 1.8 | |
| average aspect ratio | 1.6 | |
| unsettled bulk density | 0.30 g/cm³ | 25 |
| Metoprolol Tartrate (active ingredient) | Mulji Mehta & Sons, India | 10 |
| DCL 11 Lactose | Pharmatose, Netherlands | 24.5 |
| Impalpable Lactose | Sheffield, USA | 30 |
| STARCH 1500 ® | Colorcon, USA | 10 |
| Magnesium Stearate | Mallinckrodt, USA | 0.5 |
| Flow property of blend: mean time to avalanche (MTA) | | 9.1 sec |

*Measured via RapidVue 5X Image Analyzer

TABLE 2

Example 1

| Ingredient | Manufacturer | Wt. % |
|---|---|---|
| Granulated METHOCEL K4M Premium CR Grade of Example 1 | The Dow Chemical Company, USA | |
| Properties of granulated METHOCEL K4M Premium CR | | |
| mean particle diameter | 270 micrometers* | |
| particle size distribution span | 1.5 | |
| average aspect ratio | 1.6 | |
| unsettled bulk density | 0.15 g/cm³ | 25 |
| Metoprolol Tartrate (active ingredient) | Mulji Mehta & Sons, India | 10 |
| DCL 11 Lactose | Pharmatose, Netherlands | 24.5 |
| Impalpable Lactose | Sheffield, USA | 30 |
| STARCH 1500 ® | Colorcon, USA | 10 |
| Magnesium Stearate | Mallinckrodt, USA | 0.5 |
| Flow property of blend: mean time to avalanche (MTA) | | 5.5 sec |

*Measured via RapidVue 5X Image Analyzer

Flows of the blends of Comparative Example A and Example 1 are measured in a commercially available AeroFlow® tester. The Aeroflow measures the avalanching behavior of the blend. A shorter time between avalanches indicates a better flowing blend. The mean time to avalanche (MTA) for the blend of Comparative Example A is 9.1 seconds and the MTA for the blend of Example 1 is 5.5 seconds. This is an indication that the blend of Example 1 comprising the granular material of the present invention has improved flow properties as compared to a corresponding blend having a corresponding excipient in fine powder form. Additional indication of the improved flowability of the blend of Example 1 is evidenced by the free flow of the material through the tablet press hopper of outlet size of 2.25" (about 5.715 cm), whereas the blend of Comparative Example A does not flow freely through the hopper and arches over the hopper outlet unless external vibration is applied.

Tablet Production

The blends described in Tables 1 and 2 are compressed into tablets according to a direct compression process. The tablets are made using a Manesty Beta Tablet Press with a target tablet weight of 400 mg each. The tooling used in the press is 10 3 mm in diameter, round, flat-faced and bevel-edged. The tablet press is set at a speed of about 17 RPM (revolutions per minute) and the tablets are compressed at a target compression force of 5000 lb (22.2 kN), producing a compaction pressure of 266 MPa. The blends are tableted with each run lasting about 40 minutes.

Each tablet is weighed using an analytical balance and then each tablet is crushed using a HT-300 Hardness Tester. Table 3 below illustrates the comparison between the blends of Comparative Example A and Example 1. The blend of Example 1 achieves the target tablet weight and shows much less tablet to tablet variability than those made from the blends of Comparative Example A. Less tablet-to-tablet variability is an indication of the superior flow properties of the material of Example 1.

Table 3 below also shows a comparison of the tablet hardness values between the two formulations. The tablet hardness of the tablets produced from the blends of Example 1 are slightly lower than of the tablets produced from the blends of Comparative Example A but the variability in tablet to tablet hardness is much lower when the tablets are produced from the blend of Example 1 than from the blend of Comparative Example A. The hardness of tablets produced from the formulation of Example 1 exceeds the value typically required by industry. A typically accepted industry value for tablet hardness is 7 kp or greater for tablets of this size. (1 kp=1 kilopond, the equivalent of the kilogram-force).

Figure 1:
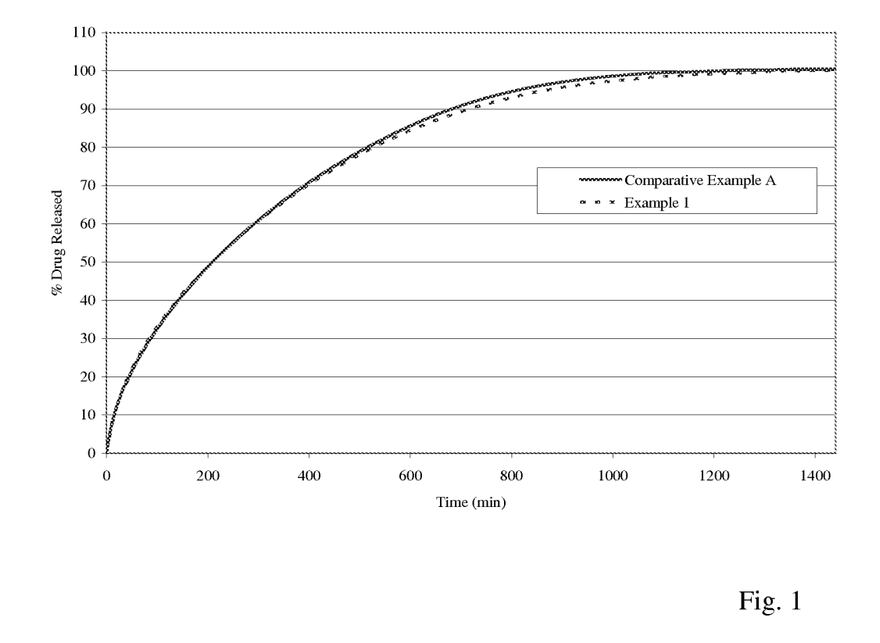
FIG. 1 illustrates the controlled release of a pharmaceutical dosage form prepared with a granular material of the present invention in comparison with a pharmaceutical dosage form prepared with a known excipient of smaller particle size.

The sustained release performances of the tablets are also compared. Controlled or sustained release of the drug metoprolol tartrate is measured using 6 tablets from each formulation. The tablets are dissolved in de-ionized water using a Varian Total Solution w/Dual VK 7025 dissolution system which is commercially available. As shown in FIG. 1 the dissolution profiles for the tablets of Comparative Example A and Example 1 nearly overlay indicating the two formulations provide the same level of controlled release performance. Additionally Table 3 shows that the amount of drug released after 5 hours for each formulation is the same.

TABLE 3

| Tablet weight | Average Weight (mg) | Standard Deviation |
|---|---|---|
| Comparative Example A | 377.8 | 31.4 |
| Example 1 | 401.0 | 4.1 |

| Tablet Hardness | Hardness (kp) | Standard Deviation |
|---|---|---|
| Comparative Example A | 13.0 | 6.2 |
| Example 1 | 12.0 | 1.7 |

| Sustained Release Properties | Time (min) | Percent Drug Released |
|---|---|---|
| Comparative Example A | 300 | 60.9 |
| Example 1 | 300 | 60.7 |

The obtained results in Comparative Example A and in Example 1 illustrate that the granular material of the present invention has improved flowability, even when blended with other ingredients of a sustained-release pharmaceutical dosage form, as compared with a corresponding excipient in fine powder form. The obtained results in Comparative Example A and in Example 1 also illustrate that the granular material of the present invention produces sustained-release pharmaceutical dosage forms such as tablets with less tablet-to-tablet variability in tablet physical properties as compared to a corresponding excipient in fine powder form. These benefits are obtained while achieving a very similar or even an essentially identical sustained drug release profile. In view of the known fact that a small particle size of the excipient is highly desirable for obtaining a sustained release profile, it is highly surprising that essentially the same sustained drug release profile can be obtained with an granular material of a considerably larger mean particle size. The mean particle diameter of the excipient of Example 1 is more than twice the mean particle diameter of the excipient of Comparative Example A in the fine powder form.

EXAMPLE 2 AND COMPARATIVE EXAMPLE B

Various granulation methods are tested.
Granulation in a Lödige Granulator
A 5-liter Lödige M5R Ploughshare mixer is used to agglomerate the METHOCEL K4M Premium CR Grade hydroxypropyl methylcellulose in the presence of water. Six hundred grams of dry material is charged to the mixer and 200 grams of water is injected and mixed with the hydroxypropyl methylcellulose for 5 minutes. To enhance mixing the main blades are run at the rate of 300 rpm and the high speed (3600 rpm) chopper blades are in operation during this wetting/agglomeration phase of the process. The wet material, containing 33 percent moisture, is dried until the moisture content is reduced to less than 4 weight percent. The main blade speed is reduced and the chopper blades are turned off during this drying phase of the process to prevent excessive break up of the granulated material.

Granulation in a High Shear Granulator
About 1.5 kg of METHOCEL K4M Premium CR Grade hydroxypropyl methylcellulose is granulated in the presence of a 2% solution of METHOCEL K3 Premium LV hydroxypropyl methylcellulose. The high shear granulator is operated using a 300 rpm main blade speed and an 1500 rpm side-chopper speed. The manufactured wet granular material is wet milled using a lab-scale CoMil equipped with a square-hole screen and operating at 1000 rpm. The wet granular material is tray-dried overnight. The dried material is dry milled using the same lab-scale CoMil equipped with a grater-type screen and operating at 1000 rpm. After milling, granules greater than 1180 microns are removed before testing.

Granulation in a Fluid Bed Granulator
The same Glatt, model GPCG-300, fluid bed system is used to granulate samples as in Example 1. Air heated to 50° C. is injected up through a disperser plate at the bottom of the cone, fluidizing the powdered hydroxypropyl methylcellulose. Water as a binding agent is injected downward through a spray nozzle (atomization pressure 30 psia) at a spray rate of 900 grams per minute into the middle of the fluid bed to wet the solid particles. After about 28 percent of water is injected, based on the weight of the dry powder, the wetted hydroxypropyl methylcellulose is dried in the fluid bed at 60° C. to a final volatiles content of less than 3 weight %. The total time for each of the runs is about 35-50 minutes.

Figure 2:
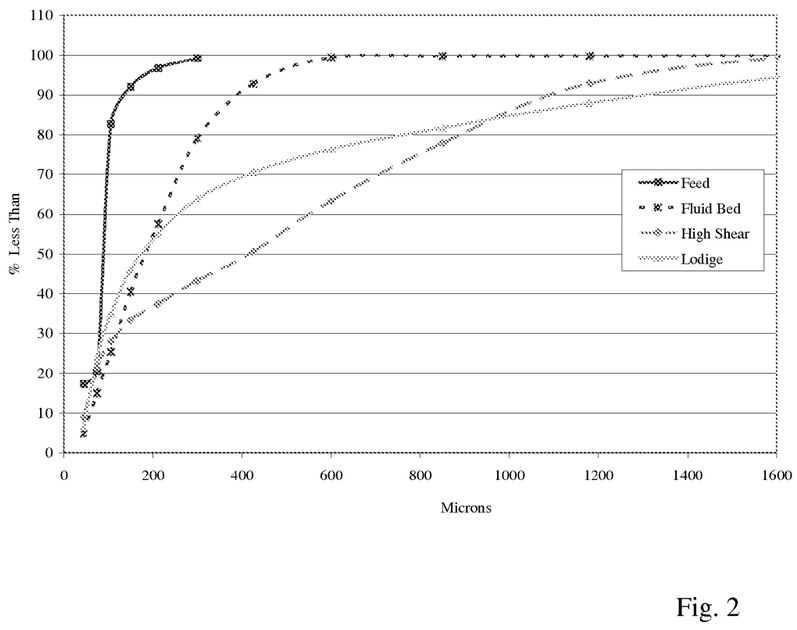
FIG. 2 illustrates the cumulative particle size distribution of a granular material granulated by various methods.

The particle size distribution of the produced granular materials is evaluated by sieve analysis using sieves of 6 mesh (screen size 3350 micrometers), 8 mesh (screen size 2360 micrometers), 12 mesh (screen size 1700 micrometers), 16 mesh (screen size 1180 micrometers), 20 mesh (screen size 850 micrometers), 30 mesh (screen size 600 micrometers), 40 mesh (screen size 425 micrometers), 50 mesh (screen size 300 micrometers), 70 mesh (screen size 212 micrometers) 100 mesh (screen size 150 micrometers), 140 mesh (106 micrometers), 200 mesh (screen size 75 micrometers) and 325 mesh (screen size 45 micrometers) respectively. The data is then plotted as the cumulative percent of material passing versus a given screen size. FIG. 2 illustrates the Cumulative Particle Size Distribution (Cumulative PSD), that is the cumulative percentage of particles that are smaller than a given size. The particle size distribution curve designated as "Feed" is the particle size distribution of a hydroxypropyl methylcellulose fine powder which is commercially available from The Dow Chemical Company under the Trademark METHOCEL K4M Premium CR Grade. The particle size distribution span is determined based on the Cumulative Particle Size Distribution as described further above.

TABLE 4

| Type of granulation | Particle Size Distribution Span |
|---|---|
| Lödige | 7.03 |
| High Shear | 2.52 |
| Fluid Bed | 1.76 |

The results in Table 4 and in FIG. 2 illustrate the narrow particle size distribution span that is obtained by the fluid bed granulation process in comparison to other particle granulation techniques.

METHOCEL K4M Premium CR Grade hydroxypropyl methylcellulose that has been granulated in a Lödige Granulator, in a High Shear Granulator and in a Fluid Bed Granulator are compressed to a compact using a single station Carver press. The target weight is 300 mg each. The compacts are compressed at a target compression force of 5000 lb (22.2 kN), producing a compaction pressure of 266 MPa. Each tablet is crushed using a HT-300 Hardness Tester to determine its hardness. The tensile strength of the compact is calculated based on the following formula: Tensile Strength=$2P/(\pi)(t)(D)$, where P=applied load, t=thickness of compact in mm , and D=diameter of the compact in mm. The applied load is the force measured by the HT-300 hardness tester at the breaking point of the compact, converted into N (Newtons). (1 $N/mm^2$=1 MPa; $\pi$=3.14159).

According to Comparative Example B compacts with target weights of 300 mg each are pressed in the same manner from a commercially available competitive polymeric material B which is purported to have good powder flow properties. The competitive polymeric material is a hydroxypropyl methylcellulose which has a methoxyl content of 19-24 percent, a hydroxypropoxyl content of 7-12 percent, a nominal viscosity of about 4000 mPa·s, a mean particle diameter of about 200 micrometers, a particle size distribution span of about 1, an average aspect ratio of about 1.6 and an unsettled bulk density of about 0.45 $g/cm^3$.

Table 5 below shows the tensile strengths of compacts pressed from the granular materials of Example 2 which have been granulated using a Lödige granulator, a high shear granulator and a fluid bed granulator as described above and compacts pressed from the commercially available competitive polymeric material B.

TABLE 5

| Materials | Compact Tensile Strength (MPa) |
| --- | --- |
| METHOCEL K4M Premium CR Grade of Comparative Example A | 3.74 |
| K4M granulated by fluid bed granulation | 2.67 |
| K4M granulated by high shear granulation | 2.24 |
| K4M granulated in a Lödige Granulator | 1.57 |

TABLE 5-continued

| Materials | Compact Tensile Strength (MPa) |
| --- | --- |
| hydroxypropyl methyl cellulose of Comparative Example B | 1.31 |

The higher tensile strength for the hydroxypropyl methylcellulose compacts made via fluid bed granulation shows the improved compactibility properties of this granular material over hydroxypropyl methylcellulose compacts made via high shear granulation and Lödige granulation which in turn show improved compactibility properties over the competitive hydroxypropyl methylcellulose material according to Comparative Example B. Compacts from the non-granulated METHOCEL K4M Premium CR Grade hydroxypropyl methyl cellulose of Comparative Example A which is used as a feed material for the various granulation methods have superior tensile strength, but the feed material in powder form has insufficient flow properties, as shown in Example 1 and Comparative Example A.

Figure 3:
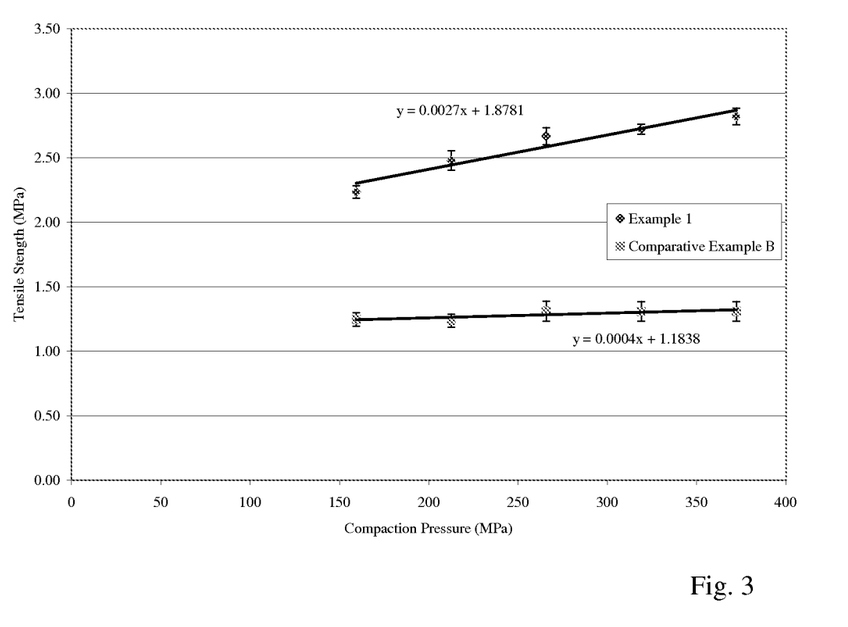
FIG. 3 illustrates the tensile strength of a compact produced from the granular material of the present invention and of a commercially available material.

FIG. 3 shows the tensile strength y of compacts as a function of the compaction pressure x for a) the granular material of the present invention made via fluid bed granulation and b) the material of Comparative Example B. FIG. 3 illustrates that the compacts made from the granular material of the present invention made via fluid bed granulation do not only have a higher tensile strength but also show a higher slope $\Delta y/\Delta x$.

The superior compactibility of the granular material of the present invention carries over with practical significance into pharmaceutical formulations as shown in Table 6 below. Pharmaceutical formulations with the compositions listed in Table 6 are prepared. Tablets from each formulation are made using a Manesty Beta Tablet Press with a target tablet weight of 400 mg each and a target compression force of 22.2 kN (5000 pounds force), producing a compaction pressure of 266 MPa. The tooling used in the press is 13/32" (10.3 mm), round, flat-faced and bevel-edged. Each tablet is weighed using an analytical balance and then each tablet is crushed using the HT-300 Hardness Tester. The hardness values shown are an average of 10 tablets.

TABLE 6

| | Tablet Hardness (kp) | Standard Deviation |
| --- | --- | --- |
| Acetaminophen Formulation (30% granular acetaminophen, 25% hydroxypropyl methylcellulose (HPMC), 34.5% DCL 11 lactose, 10% STARCH 1500 ®, 0.5% magnesium stearate) | | |
| HPMC is K4M granulated by fluid bed granulation | 6.9 | 0.6 |
| HPMC is the hydroxypropyl methylcellulose of Comparative Example B | 4.0 | 0.4 |
| Metoprolol Tartrate Formulations (10% metoprolol tartrate, 25% HPMC, 24.5% DCL 11 lactose, 30% impalpable lactose, 10% STARCH 1500 ®, 0.5% magnesium stearate) | | |
| HPMC is K4M granulated by fluid bed granulation | 14.3 | 0.8 |
| HPMC is the hydroxypropyl methylcellulose of Comparative Example B | 7.7 | 0.5 |

What is claimed is:

1. A granular material having a mean particle diameter of 250 to 350 micrometers and a compactibility resulting in a compact with a tensile strength of at least 1.7 MPa when the granular material is subjected to a compaction pressure of 266 MPa, at least 80 percent of the granular material being a water-soluble cellulose ether, water-soluble cellulose ester, an alkylene oxide homo- or copolymer or a blend thereof, wherein the granular material has been obtained by subjecting the water-soluble cellulose ether, water-soluble cellulose ester, alkylene oxide homo- or copolymer or blend thereof in powder form to a granulation step.

2. The granular material of claim 1 having an unsettled bulk density of 0.1 to 0.35 g/cm$^3$.

3. The granular material of claim 1 having a particle size distribution span of 0.75 to 4.

4. The granular material of claim 3 having a particle size distribution span of 1 to 2.

5. The granular material of claim 1 having an average aspect ratio of 1 to 2.

6. The granular material of claim 1 having a compactibility which results in a compact with a tensile strength of 2 to 4 MPa when the granular material is subjected to a compaction pressure of 266 MPa.

7. The granular material of claim 1 having an unsettled bulk density of 0.15 to 0.25 g/cm$^3$.

8. The granular material of claim 1 being an excipient for a dosage form.

9. The granular material of claim 8 being an excipient for a sustained-release dosage form.

10. The granular material of claim 1 wherein the water-soluble cellulose ether is a hydroxypropyl methyl cellulose having a hydroxypropoxyl substitution of 4 to 12 percent and a methoxyl substitution of 19 to 30 percent.

11. A direct compression process for preparing a dosage form comprising the step of
   a.) blending an active ingredient, the granular material of claim 1 and one or more optional adjuvants in the absence of a substantial amount of added solvent or heat, and
   b.) compressing the resulting composition to a dosage form.

12. A process for granulating a polymer powder comprising the step of granulating in a fluid bed granulator a water-soluble cellulose ether, water-soluble cellulose ester, an alkylene oxide homo- or copolymer or a blend thereof to produce the granular material of claim 1.

13. A granular material having a mean particle diameter of 250 to 350 micrometers, a particle size distribution span of 1 to 2 and a compactibility resulting in a compact with a tensile strength of at least 1.7 MPa when the granular material is subjected to a compaction pressure of 266 MPa, at least 90 percent of the granular material being a hydroxypropyl methyl cellulose having a hydroxypropoxyl substitution of 4 to 12 percent and a methoxyl substitution of 19 to 30 percent, wherein the granular material has been obtained by subjecting the hydroxypropyl methyl cellulose in powder form to a granulation step.

* * * * *